United States Patent
Zanin

[11] Patent Number: 6,129,665
[45] Date of Patent: Oct. 10, 2000

[54] ELECTRO-MEDICAL APPARATUS

[75] Inventor: Simone Zanin, Veneto, Italy

[73] Assignee: Biotekna S.r.l, Cimpello di Fiume Veneto, Italy

[21] Appl. No.: 09/147,326

[22] PCT Filed: May 26, 1997

[86] PCT No.: PCT/IT97/00118

§ 371 Date: Nov. 27, 1998

§ 102(e) Date: Nov. 27, 1998

[87] PCT Pub. No.: WO97/45056

PCT Pub. Date: Dec. 4, 1997

[30] Foreign Application Priority Data

May 31, 1996 [IT] Italy .................................. 96A000088

[51] Int. Cl.⁷ .................................................. A61B 5/04
[52] U.S. Cl. .......................................................... 600/346
[58] Field of Search ................................... 600/546, 554; 128/923, 924, 925

[56] References Cited

U.S. PATENT DOCUMENTS

| | | | |
|---|---|---|---|
| 5,313,956 | 5/1994 | Knutsson et al. | 600/554 |
| 5,540,235 | 7/1996 | Wilson | 600/554 |
| 5,590,665 | 1/1997 | Kanai | 128/925 |

*Primary Examiner*—William E. Kamm
*Attorney, Agent, or Firm*—Oblon, Spivak, McClelland, Maier & Neustadt, P.C.

[57] ABSTRACT

An electro-medical apparatus for receiving bio-electrical signals from a human body. At least 17 electrodes are applied to specific areas of the body of the patient. The signals received therein are automatically processed by a personal computer which analyzes the health state of the patient by way of specific software. An expert system can additionally be included which includes control software, analysis software and interpretation software to provide the physician with first indication data about the health of the patient and with possible modes of intervention, so that the physician can arrive at a substantially definitive interpretation of the health state of the patient.

9 Claims, 2 Drawing Sheets

ELECTRO-MEDICAL APPARATUS

BACKGROUND OF THE INVENTION

1. Field of the Invention

The present invention relates to an electro-medical apparatus comprising a plurality of electrodes, which are adapted to receive bio-electrical signals emitted by an individual, in correspondence of specific areas of his body and comprising means for collecting data collected by the electrodes, so that said signals could be analyzed and a substantially objective evaluation of the equilibrium of the body functions at the level of said specific areas could be performed.

2. Discussion of the Background

For decades, engineers have attempted to facilitate the analysis and the diagnosis of the human body functions as well as to help physicians in the objective evaluation of the patient's health.

It has been about twenty years since German physicians were able to acquire the bio-electrical signals, which are emitted in correspondence of specific areas of the human body, and so they obtained from these data bio-electrical information of an individual, who is examined by a physician. It is well known that the human body emits electrical signals in correspondence of its specific areas. Said signals, duly picked-up and amplified, allow to translate the signals (microampere, microvolt, ohm, conductance, frequency, etc.) into data, which are related to the more or less normal equilibirum of the examinated individual.

The first apparatuses, which were conceived in Germany, would analyze the bio-electrical state of seven areas of the human body, as well as proceed in the reading of the electrical potential, stimulate the measure area with a 10 Hz. impulse package in order to remeasure the conduttance in that area, to make the passive reading of the (inverse) current discharge, stimulate again the measure area with an inverted current impulses, read again the value of said current and therefore of the electrical potential. Said current was repeated seven times on seven human body areas.

The information, which was collected from the seven analyzed areas, had to to be evaluated according to a substantially objective way from the physician, who had used the bio-medical apparatus. The important fact was made of the method, which allowed to use the bio-electronic information and allowed to make a diagnostic interpretation. Already at the time the collected information should be based on a statistic interpretation, but it was recognized that this information would prove the normality or the abnormality of a certain area of the body, for instance the patient's head.

It should be pointed out that the electromedical apparatuses, which were first manufactured in Germany, were able to give the physician a series of data, which were then translated into graphics. These graphics were rather difficult to decipher, whereby at least some years were necessary for the physician to approximately interpret these data.

The German manufacturers of said apparatuses arrived to a considerable sophistication as far as the electrical data measure in some human body areas is concerned, as well as to involve acupuncture therapies, Chinese medicine, etc. But they limited themselves to substantially decode the electrical data of these measures and to simplify their interpretation.

In the U.S.A. the analysis technique of electrical potentials has been used mainly as encephalograms, sleep state measurement, and so on, but not as bio-functional measures, i.e. the measures, which provide elements for arriving to a certain diagnosis and to say, on the collected data basis, whether a certain organ of the human body is working or not and how much this working departs from a normal state.

Meanwhile it is to be pointed out that said bio-functional measures present a further important advantage, i.e. they can record according to a specific way the health state of an individual and a further analysis, which confirm the same data, should just correspond to the same individual and never to another one.

As for Japan, they just started to develop a similar apparatus and we would likely learn quite soon interesting news in the field of the bio-electronic.

The German school of the bio-functional measures has achieved up to indicate the electrical signals (conductance, current, etc.), which are present in correspondence of specific areas of the human body and suggest, by comparison and by survey, a rather reduced interpretation of the collected data. It could be a further big success for the producers of such an apparatus to use it after a shorter time, which is requested for a good training even with the help of a data bank.

In general, physicians who use a scientific apparatus require that the same apparatus should give the elements of a certain result, i.e. of a certain diagnosis, whereas the same physicians intend to arrive to definitive diagnostic conclusions. Therefore, what is important is that apparatus could supply a certain outline, whereas the physician should verify the outline which is given by the apparatus.

On the basis of the collected data, which are not subjected in Germany to particular processing or decoding, further measures could suggest to the physician the possible patient change of state, whereby the most critical point depends on the results of the first examination, because it is much easier to make a comparison of the data collected later on with the data previously collected.

In order to summarize what up to now was explained, the similar German apparatuses provide data, which are often subject to a difficult, subjective interpretation, whereby a risk is present in the possibility of errors in such an interpretation.

As for the safety of these apparatuses, the German ones are generally working with a power supply of 220 V. 50 Hz., which could affect the patient state and the response of the apparatus. In the field of the bio-electronics the energy supply should be substantially insulated. The signal, which is emitted by the apparatuses, should be quite clean, whereas the German ones don't respect such a requirement because they were conceived about 20 years ago, when the microelectronics was not in the condition to give substantially better resolutions.

The interpretation of the tests, which were carried out by the German apparatuses, was depending on the diagram plotted on a sheet of paper, with no reference to digital values for a rather quantitative interpretation of the data.

The main problem, which the apparatus according to the invention intends to solve, is to propose an instrument of the bio-energetical-functional type, which should be able to evaluate whether and to what extent the various organs or systems of the patient are working how much they depart from the optimum conditions, which organ or system could be the origin of the problem and, at last, how to prevent such deviations from the optimum conditions.

It should be observed that at least two different schools are present in the medical field: the first one belongs to the classic school, which suggests after ascertaining the presence of a disease to intervene in order to eliminate the disease. The bio-energetical-functional school does trouble to establish the presence of an abnormal state, but mainly it does trouble how much the present state of the patient is departing from a normal state, as well as when and according to which extent the patient is improving during and after a therapy. The bio-electronical science intends to prevent and to monitor the therapy through a well-timed and continuous control of the evolutive and involutive patient state.

SUMMARY OF THE INVENTION

This problem is solved by the apparatus according to the invention, which is characterized by at least seventeen areas of the human body on which the electrodes are able to operate through the data collection, in order to confine substantially narrower human body areas and consequently to increase the passage tracks of the collected information, means being provided for a substantially automated processing of the collected data.

A further goal of the apparatus according to the invention intends to reach is to decode within real times and according to substantially reliable way the bio-electrical information collected by the apparatus so as to help the physician by providing him with substantially more detailed data.

This problem is solved by the apparatus according to the invention, which is characaterized in that it is able to substantially decode and to process all the bio-electrical information which are provided by the electrodes and to present them according to a digital shape, so that the software of the PC could analyze the health state of the patient by leaving aside the necessity of graphs, charts and similar objects.

Another advantage of the present invention is the opportunity to analyze the patient's health state organ by organ. Specifically, the present invention permits comparing any specific situation with a series of data statistically collected from a data bank, so that the physician could evaluate the criticality of a particular situation, said situation being able to be related with other specific situations.

The above advantages are provided by the apparatus according to the invention, which is characterized by at least an "expert system" which comprises at least a control software adapted to control the same apparatus, a analysis software adapted to decode the electrical information collected from the various areas of the body and to translate them into graphs and an interpretation software adapted to provide the physician with first indication data about the health state of the patient and with possible modes of intervention, in order to allow the physician to arrive to a substantially definitive interpretation of the health state of the patient.

BRIEF DESCRIPTION OF THE DRAWINGS

Said and further features of the invention will be apparent from the following description and from the accompanying drawings, where.

DETAILED DESCRIPTION OF THE PREFERRED EMBODIMENTS

Figure 3:
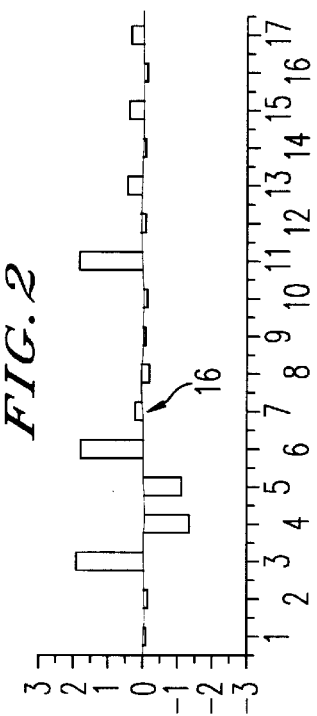
FIG. 3 represents a humanoid provided with the areas which were subjected to reading.
Figure 1:
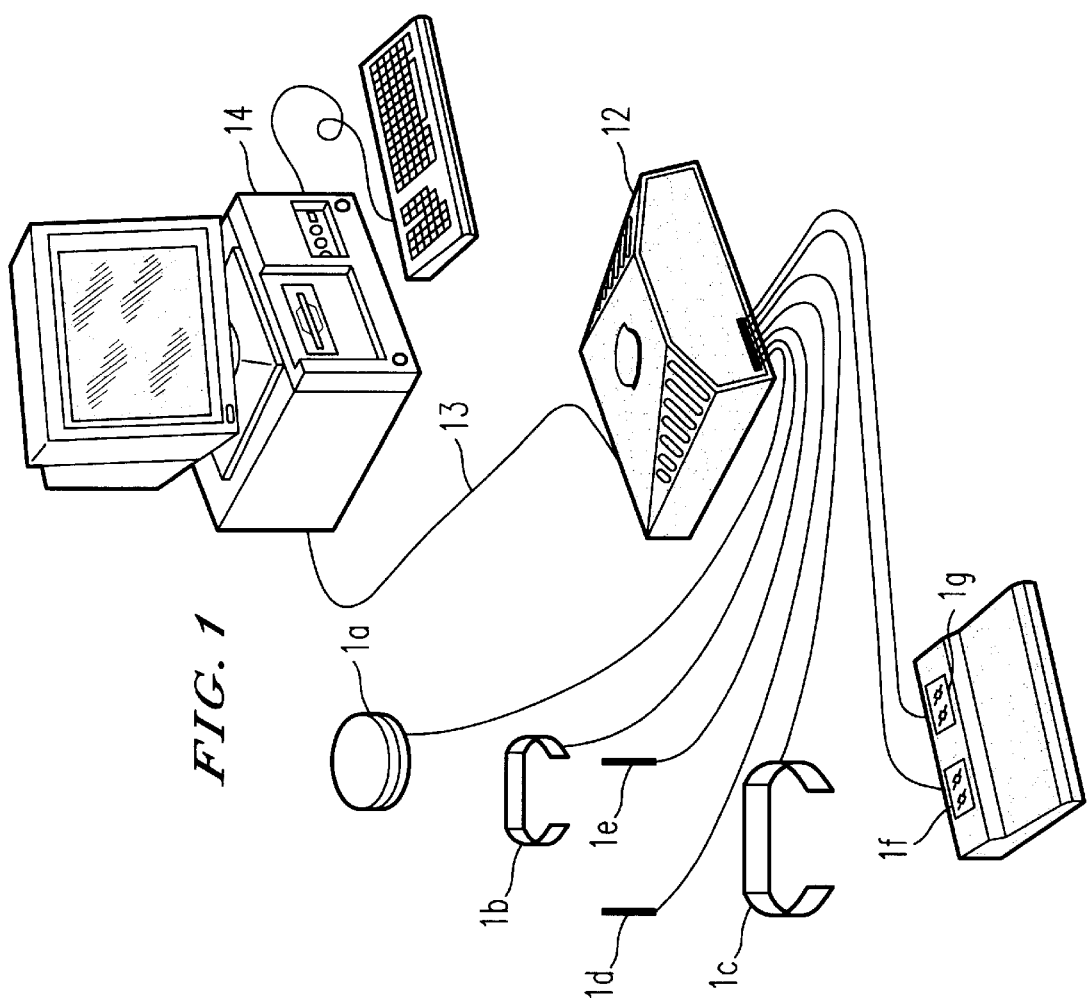
FIG. 1 represents a schematic perspective view of the apparatus according to the invention.

The apparatus according to the invention comprises a plurality of electrodes $1a,1b,1c,1d,1e,1f,1g$ which are adapted to be applied in various areas of a human body of FIG. 3 (3=right arm, 4=the right part of pelvis, 5=the right leg, 1=the head, 11=the left leg). The electrode $1a$ is to be applied to the head, the electrodes $1b,1c$ are to be applied to the arms and to the legs, respectively right and left, the electrodes $1d,1e$ to the respectively right and left body parts, the electrodes $1f,1g$ to the respectively right and left foot.

Figure 2:
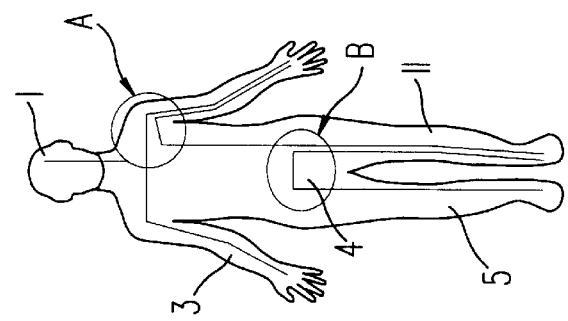
FIG. 2 represents a sample of bipolar graph processed by the apparatus.

The electrical signals of the various body areas are collected by a hardware 12, which as it will be apparent later on the signals are addressed to the software of a PC 14 so that they can processed and reported on a bipolar graph 16 (FIG. 2). In such a graph the data are processed by the PC, are separated according to each examined area (the areas are seventeen) along the abscissa, whereas the ordinate represents the positive and negative values for each examined area. The positive values represent over-values and the negative values the under-values.

The apparatus according to the invention operates according to the following way.

the values of the electrical tension are detected in correspondence of the seventeen areas of the human body, whereby the relevant situation of these areas is stored in the hardware 12;

later the various areas are stimulated with a low electrical voltage having a frequency of about 13 Hz; the response is recorded;

at first the feet of the patient are involved, which are put on the electrodes $1f,1g$. In such a way the organism is excited in order to bring the patient to an active bio-electrical level. Thanks to the low electrical voltage having a frequency of about 13 Hz, the patient could become diagnosable. Indeed the patient's conditions vary hour by hour during the day, whereby the reading of the detected values could substantially vary during the day. In the German apparatus the patient is subjected to a shock from temperature or from pain;

the feet are subjected to a positive and then negative value of the electrical tension, in order to depolarize the excited area, during 13 sec.

The graph of FIG. 2 reveals the maximum bio-energetical over-alteration in correspondence of the areas 3,6,11, whereas it reveals the minimum bio-energetical underalteration ion correspondence of the areas 4,5. The circles A,B of the humanoid represent respectively the two detected areas as abnormal areas.

The described apparatus is also able to provide samples of uni-polar graphs, which are not represented in the drawings. In addition the hardware 12 should be controlled by and should be directly depending on the PC 14, which practically is not autonomous. Indeed also the hardware 12 is internally provided of a software, which is not represented in the drawings. The hardware 12 and the PC 14 are able to dialogue each one with the other through the interface in the hardware 12. For instance if a value of electrical tension is read in the area 1 (FIG. 2), this value is read and stored in the hardware 12, which is transducted into a digital language in order to send it to the PC.

Figure 4:
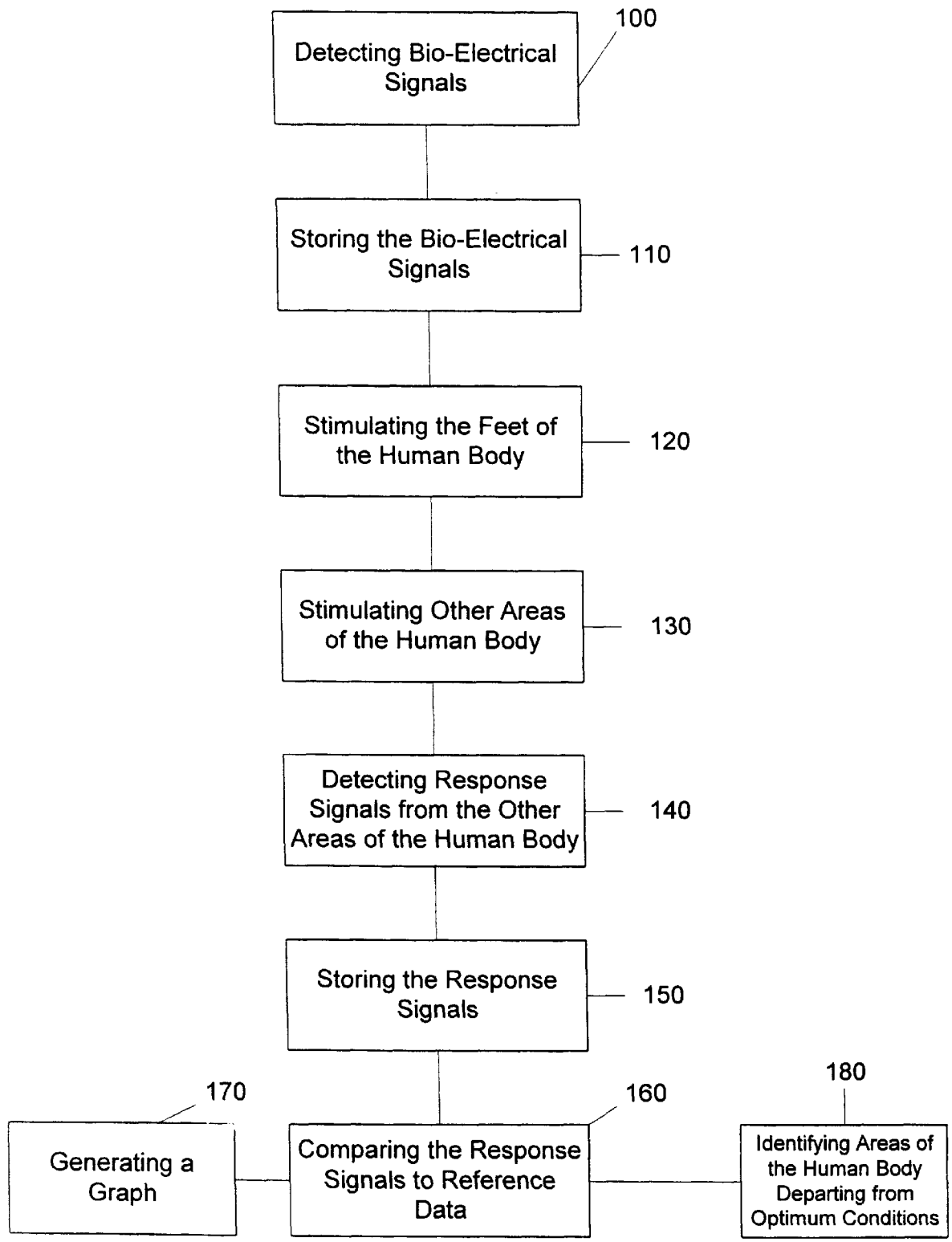
FIG. 4 represents a flowchart of a method of obtaining information from a human body according to the present invention.

As shown in FIG. 4, the logical sequence of the process practically provides the following phases:

all the values of electrical tension of the various areas are detected (step 100) and stored (step 110) into the hardware 12;

the patient is stimulated in correspondence of his feet with a low electrical voltage having a frequency of about 13 Hz (step 120) so that the test could become objective after the patient has obtained substantially optimum bio-electrical condition;

in correspondence of each one of the seventeen areas a stimulus is emitted (step 130) and the reply is stored (step 140 and 150) as a whole for one first and a second time;

after stored all the digital information, such an information is stored in a so-called "expert system" which analyzes the digital data. Such an analysis is carried out by said "system" for a comparison with the statistical data (step 160), which were collected during the last 20 years, and which allow to ascertain whether the digital data are comprised into the ranges or not. Such an "expert system" comprises at least a control software, which controls the hardware 12, an analysis software, which decodes the electrical information collected in the various areas of the body and represents them in mono- or bi-polar graphs (step 170), and at last an interpretation software, which provides the physician a first indication of the patient health state. Such a software practically represents the software of the PC 14;

the PC processes the mono- or bi-polar graphs, so that the areas, which are affected by a bio-energectical-functional excess or lack;

the information, which are represented by the test data, allow to process the diagrams for the interpretation of the various parameters obtained in correspondence of the seventeen areas (oxygen, PH, functional blocks, energetical level, inflamation level, toxin presence, chronicity level in correspondence of the various measure levels, etc.).

In conclusion the apparatus according to the invention allows thanks to the hardware 12 the automatic processing of the collected data, and avoids the risk of a subjective interpretation, for instance the interpretation carried out with the German apparatuses, which are providing plotted graphs on paper sheets.

Also the safety is ensured because the power supply 220 V, 50 Hz, is eliminated, which can negatively affect the health state of the patient and the working of the apparatus, which can now work thanks to a power supply made of 12V. batteries. In such a way, the data collection and processing, as well as the test quality are ensured.

At last, the apparatus according to the invention provides a bio-energetical-functional instrument, which can verify whether, and according to which extent, the various organs or systems of the patient are working well or not (step 180), and how much they depart from optimum conditions, which organ or system could be the origin of the problem and how to prevent the deviation from optimum conditions.

What is claimed is:

1. A method for obtaining information from a human body, comprising the steps of:

detecting values of bio-electrical signals emitted from a plurality of areas of said human body;

storing said values of bio-electrical signals in a processor;

stimulating the feet of said human body with a low electrical voltage;

stimulating said plurality of areas with a low electrical voltage;

detecting response signals from said plurality of areas; and storing said response signals.

2. The method of claim 1, further comprising the step of:

comparing said response signals with reference data.

3. The method of claim 2, wherein the step of comparing said response signals with said reference data is performed by said processor using a software.

4. The method of claim 3, wherein the step of stimulating the feet is performed by applying an electrical voltage of not more than 5V.

5. The method of claim 4, wherein the step of stimulating the feet is performed by applying an electrical voltage having a frequency of about 13 Hz.

6. The method of claim 5, wherein the step of stimulating the plurality of areas is performed by applying an electrical voltage of not more than 5V.

7. The method of claim 6, wherein the step of stimulating the plurality of areas is performed by applying an electrical voltage having a frequency of about 13 Hz.

8. The method of claim 7, further comprising the step of:

generating a graph representing responses from said plurality of areas of the human body.

9. The method of claim 7, further comprising the step of:

identifying areas of the human body that depart from optimum conditions based on said response signals.

* * * * *